US009186111B2

(12) United States Patent
Jeanne et al.

(10) Patent No.: US 9,186,111 B2
(45) Date of Patent: Nov. 17, 2015

(54) SYSTEM AND METHOD FOR CONVERTING AN INPUT SIGNAL INTO AN OUTPUT SIGNAL

(75) Inventors: Vincent Jeanne, Eindhoven (NL); Nathalie Velthoven, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/880,408

(22) PCT Filed: Nov. 9, 2011

(86) PCT No.: PCT/IB2011/055000
§ 371 (c)(1),
(2), (4) Date: Apr. 19, 2013

(87) PCT Pub. No.: WO2012/066454
PCT Pub. Date: May 24, 2012

(65) Prior Publication Data
US 2013/0226007 A1  Aug. 29, 2013

(30) Foreign Application Priority Data
Nov. 17, 2010  (EP) .................................. 10191480

(51) Int. Cl.
G06K 9/00 (2006.01)
A61B 5/00 (2006.01)
A61B 6/00 (2006.01)
A61B 5/0205 (2006.01)

(52) U.S. Cl.
CPC ............. *A61B 5/7278* (2013.01); *A61B 5/0075* (2013.01); *A61B 5/0205* (2013.01); *A61B 6/5288* (2013.01); *G06K 9/00503* (2013.01)

(58) Field of Classification Search
None
See application file for complete search history.

(56) References Cited

U.S. PATENT DOCUMENTS

| 6,067,399 | A | 5/2000 | Berger | |
| 8,666,116 | B2* | 3/2014 | Kirenko et al. | 382/103 |
| 2002/0171551 | A1* | 11/2002 | Eshelman et al. | 340/573.1 |
| 2004/0218789 | A1* | 11/2004 | Polcha et al. | 382/124 |
| 2005/0113673 | A1 | 5/2005 | Avinash et al. | |
| 2005/0113674 | A1 | 5/2005 | Salla et al. | |
| 2006/0058683 | A1* | 3/2006 | Chance | 600/476 |
| 2006/0133651 | A1* | 6/2006 | Polcha et al. | 382/115 |
| 2006/0241718 | A1* | 10/2006 | Tyler et al. | 607/45 |
| 2008/0045847 | A1* | 2/2008 | Farag et al. | 600/500 |
| 2008/0161661 | A1* | 7/2008 | Gizewski | 600/306 |
| 2008/0292151 | A1* | 11/2008 | Kurtz et al. | 382/128 |

(Continued)

FOREIGN PATENT DOCUMENTS

| CN | 1527992 A | 9/2004 |
| JP | 07124124 A | 5/1995 |

(Continued)

*Primary Examiner* — Tsung-Yin Tsai

(57) ABSTRACT

A system and a method for processing data obtained from an input signal including physiological information representative of at least one at least partially periodic vital signal. The physiological information is derivable from visible radiation reflected by an object. The system includes a detector for detecting at least one vital signature in the input signal and a converter for creating an output signal by modifying the input signal depending on the detected vital signature. The output signal includes an artificial signature at least partially replacing a respective vital signature of the at least one vital signature of the input signal. The system may further include a sensor for detecting visible electromagnetic radiation within at least one particular wavelength range.

20 Claims, 6 Drawing Sheets

(56) References Cited

U.S. PATENT DOCUMENTS

| | | | |
|---|---|---|---|
| 2008/0294013 A1* | 11/2008 | Gobeyn et al. | 600/300 |
| 2008/0294018 A1* | 11/2008 | Kurtz et al. | 600/301 |
| 2009/0012433 A1* | 1/2009 | Fernstrom et al. | 600/593 |
| 2009/0141124 A1* | 6/2009 | Liu et al. | 348/65 |
| 2009/0226071 A1* | 9/2009 | Schuler et al. | 382/133 |
| 2009/0306484 A1* | 12/2009 | Kurtz et al. | 600/300 |
| 2010/0036676 A1* | 2/2010 | Safdi et al. | 705/2 |
| 2010/0041968 A1 | 2/2010 | Meschisen et al. | |
| 2010/0061596 A1* | 3/2010 | Mostafavi et al. | 382/107 |
| 2010/0198112 A1 | 8/2010 | Maad | |
| 2010/0238294 A1* | 9/2010 | Hogasten et al. | 348/164 |
| 2010/0309300 A1* | 12/2010 | Chhibber et al. | 348/77 |
| 2014/0086462 A1* | 3/2014 | Shan et al. | 382/128 |
| 2014/0180132 A1* | 6/2014 | Shan et al. | 600/476 |

FOREIGN PATENT DOCUMENTS

| | | |
|---|---|---|
| JP | 2003146107 A | 5/2003 |
| WO | 2008010275 A1 | 1/2008 |
| WO | 2010071738 A1 | 6/2010 |
| WO | 2010100594 A2 | 9/2010 |
| WO | 2011042839 A1 | 4/2011 |

\* cited by examiner

SYSTEM AND METHOD FOR CONVERTING AN INPUT SIGNAL INTO AN OUTPUT SIGNAL

FIELD OF THE INVENTION

The present invention relates to a system and a method for processing data for converting an input signal into an output signal, wherein the input signal comprises physiological information derivable from electromagnetic radiation, in particular from a sequence of image frames. Further, the present invention relates to a computer program for implementing said method.

BACKGROUND OF THE INVENTION

Recently, in the field of image processing enormous progress was made in that, besides the mere representation of recorded images, profound analyses of the recorded data were enabled. In particular, when recorded data comprises representations of living beings, such as animals or even, more particularly, human beings, conclusions regarding the personality or even the well-being of the individual can be enabled.

In this context, U.S. Pat. No. 6,067,399 A discloses a method and an apparatus for recording video data. The method comprises the steps of receiving unrecorded video data representative of a subject; detecting skin tone detail of said subject; manipulating said video data corresponding substantially only to said detected skin tone detail to obscure said video data corresponding to said detected skin tone detail; and recording said video data including said manipulated video data.

Hence, it is enabled to ensure the privacy of the identity of a recorded subject by masking respective parts of the subject in the recorded video data.

However, such a rigorous masking is inapplicable when it is required or desired to recognize the subject, such as a human being, at least to a certain extent. These needs can exist, by way of example, in the field of video conferencing, security monitoring, health monitoring etc.

A further challenge is related to the fact that meanwhile images and sequences thereof are digitally recorded, processed and reproduced, and can be duplicated without loss. As a result, an increased risk of a loss of control of personal information might arise.

SUMMARY OF THE INVENTION

It is an object of the present invention to provide a system and a method for processing data addressing the above-mentioned drawbacks and enabling a representation and circulation of recorded data while preserving a certain level of privacy, and while still allowing a certain level of human perception of the processed data when represented.

Furthermore, it would be advantageous to provide a system enabling recording of data while, substantially simultaneous, ensuring a processing of recorded data addressed to privacy preservation measures, and while also preventing an unauthorized access to preprocessed recorded data.

In a first aspect of the present invention a system for processing data obtained from an input signal comprising physiological information is presented, wherein the physiological information is derivable from visible radiation reflected by an object, the physiological information being representative of at least one at least partially periodic vital signal, the system comprising:

a detector means for detecting at least one vital signature in the input signal, the at least one vital signature varying over time and corresponding to the at least one at least partially periodic vital signal, a converter means for creating an output signal by modifying the input signal depending on the detected vital signature, wherein the output signal comprises an artificial signature at least partially replacing a respective vital signature of the at least one vital signature of the input signal.

The invention is based on the idea that the physiological information which is subjected to be analyzed in order to extract certain personal information therefrom can be modified without substantially affecting an overall perceptibility of the recorded object. Overall perceptibility shall be understood as referring to a general visual perceptibility of a human being. In other words, it is taken advantage of the fact that, in general, human eyesight is far less developed in this context than recognition and processing based on digital logic algorithms and operations, e.g. digital image processing.

Hence, sophisticated methods and devices for image processing can be exploited in that they are utilized in a manner diametrically opposed to their originally intended use, namely for detecting physiological information to be subjected to analyses and for modifying it in a way as to permit, or, at least, affect or influence further subsequent analysis thereof. It goes without saying that a modification of the input signal resulting in an output signal can also comprise a removal or elimination of the at least one vital signature in that the created artificial signature can be considered a blank signature.

After the recorded data is being processed, a user may forward, copy or share it without risking an uncovering of an intimate level of privacy of the recorded object of interest, namely the recorded living being, or, in particular, the recorded human being.

An example of how information can be extracted from recorded image data of living beings is described in WO 2010/100594 A2. This document discloses a method of processing images of at least one living being, including obtaining a sequence of digital images taken at consecutive points in time; selecting at least one measurement zone comprising a plurality of image points, wherein the step of selecting at least one measurement zone includes analyzing information based on pixel data of a plurality of image parts in at least one of the images, each image part including at least one image point, and selecting each measurement zone from contiguous parts determined to have similar characteristics; and for each measurement zone, obtaining a signal representative of at least variations in a time-varying average value of a combination of pixel values at at least a number of the image points for use in determining at least one of a presence and a frequency value of at least one peak in a spectrum of the signal corresponding to a frequency of a periodic physiological phenomenon. Several embodiments of how to improve the detection of the desired values are also disclosed in this document.

There exist several embodiments of the detector means and the converter means. In a first, fairly simple embodiment both the detector means and the converter means are embodied by a processing unit, in particular a processing unit of a personal computer, which is driven by respective logic commands. Such a processing unit may comprise also suitable input and output interfaces.

However, in the alternative, each of the detector means and the converter means can be embodied by a separate processing unit driven or drivable by respective commands. Hence, each respective processing unit can be adapted to its special purpose. Consequently, a distribution of tasks may be applied, wherein distinct tasks are processed, for instance, executed on a single processor of a multi-processor processing unit, or, again referring to a personal computer, image processing-related tasks are executed on an image processor while other operational tasks are executed on a central processing unit.

According to a preferred embodiment of the system for processing data the input signal comprises a continuous or discrete sequence of image frames related to a specific signal space.

According to an even further embodiment of the system for processing data the at least one at least partially periodic vital signal is selected from the group consisting of heart rate, respiration rate, and heart rate variability. Hence, it can be envisaged to modify each vital signal, or, if required, merely a single desired vital signal while leaving another vital signal basically unmodified.

Such vital information can be obtained from slight variations of, by way of example, skin tone details over time. Blood circulation and respiration are correlated with slightest changes of skin color, particularly when focusing vasculature. When capturing a sequence of image frames of an area of interest indicative of the desired skin color changes to be detected the variations over time can be excluded and assessed by means of logic algorithms, even though the changes cannot be detected by a person watching a playback of the recorded sequence of image frames by means of human perceptibility.

Thus, forwarding or distributing of unprocessed video data or the like substantially may bear the risk of unintentionally providing personal information to other parties. It could be intended to misuse such data and information extracted therefrom, e.g. for assessing the physical health or mental health of the recorded person.

According to an even further embodiment of the system for processing data the detector means is adapted to detect temporal variations of the at least one vital signature, the temporal variations being indicative of the at least one at least partially periodic vital signal.

This embodiment is preferably further developed such that the converter means comprises a submeans selected from the group consisting of a leveling means for leveling the temporal variations of the at least one vital signature, a mask means for removing the at least one vital signature from the input signal, an evaluation facilitating means for enhancing the amplitude of the vital signal indicative of temporal variations of the at least one vital signature, and a modulator means for modifying the temporal variations of the at least one vital signature, the modulator means being adapted for applying a frequency modification to the temporal variations.

There exist various embodiments of the submeans associated with the converter means. It goes without saying that the submeans also can be embodied by a processing unit driven by respective logic commands.

When the submeans is configured as a leveling means the temporal variations of the at least one vital signature can be planed in a way as to prevent a subsequent analyzing process from isolating the desired information from the recorded data. In other words, when applying, for instance, a heart rate analysis to the processed data, a zero-signal could be detected on which no further analysis can be based.

It should be understood that the leveling or planing is substantially directed to align the detected variations indicative of the at least one at least partially periodic vital signal with overall variations of the whole image frame over time. The so-called overall variations can be induced by changes of local conditions or illumination, or, in general, by noise signals. In this respect, the output signal is not completely leveled but rather no longer overlaid by the additional temporal variations enabling the extraction of the vital signal. The variations of the at least partially periodic vital signal are very small compared to the general noise-induced overall variation. By way of example, the ratio therebetween can be less than about 5:100 to less than about 1:100 in regard of the signal level variations.

It should be also understood that no complete leveling of the temporal variations of the at least one vital signature is required as even a leveling to a certain extent is considered to be sufficient to preserve the required level of privacy. Even when slight amplitudes of the desired signal would remain, an extraction of the signal can be sufficiently impeded.

The other way round, when the submeans is configured as an evaluation facilitating means, it can be envisaged to superelevate the detected temporal variations indicative of the at least one at least partially periodic vital signal. Hence, the signal to noise ratio can be improved in order to facilitate a subsequent determination of the desired vital signal.

Alternatively, the submeans can be configured as a mask means which is adapted for replacing the temporal variations of the at least one vital signature by generally constant values. The mask means and the leveling means are different from each other in that the mask means is not adapted for leveling the temporal variations of the at least one vital signature by aligning it with the overall variations of the image frame, but rather by replacing it by values not significantly aligned with or influenced by the overall variations.

In other words, for instance, when masking the face of a person recorded with the mask means a "china doll" face impression could be perceived by an observer. That is, at the level of image pixels pixel values associated with a skin portion to be analyzed (and subjected to vary over time in the input signal due to the temporal variations of the at least one at least partially periodic vital signal and, to a greater extent, to overall noise) are replaced by pixel values, e.g. of a typical skin color, generally constant or steady over time.

It is also preferred if the submeans is configured as a modulator means which might be applied to "fake" the desired vital signal. By modifying the frequency of the temporal variations an artificial vital signal is generated which can be extracted during subsequent analyzing activities but, however, does not enable to grasp the original vital signature.

An effective preservation of a certain level of privacy also can be achieved by this measure. It can be envisaged to replace the original frequency by a set frequency or by a frequency varying over time, thereby imitating a natural frequency graph.

According to a further preferred embodiment the converter means comprises an overall converter for varying a major portion of the image frames, the major portion also comprising a non-indicative signature, wherein the overall converter is preferably adapted for applying a destructive modulation to the temporal variations of the at least one vital signature. Moreover, the modulation can comprise a spatial or temporal modification of input signal components.

Needless to say, the major portion of the image frame comprises the at least one vital signature besides the non-indicative signature. In this embodiment it is further preferred that the destructive modulation comprises a multi mixing of image components which is further preferred carried out in a random manner. However, also the destructive modulation preferably is to be limited to a certain extent, namely to a level still allowing a recognition of image objects by a human observer.

According to still a further preferred embodiment the converter means is adapted to apply a multi stage conversion to the at least one vital signature.

By way of example, the multi stage conversion can comprise a frequency modification applied to the temporal variations of the at least one vital signature carried out by the modulator means and a subsequent mask operation for removing the (remainder of the) at least one vital signature carried out by the mask means. For enhancing the level of privacy preservation a further process, for instance, a destructive modulation carried out by the overall converter, can be applied. In this context, it can be also envisaged to apply a random multi stage conversion or a fixed stage sequence conversion to the input signal.

According to a preferred embodiment the system for processing data further comprises a sensor means for detecting a visible electromagnetic radiation within at least one particular wavelength range selected from the group consisting of visible light, infrared light, and ultraviolet radiation, the sensor means being connectable to the input channel.

There exist various embodiments of the sensor means. In a first, simple embodiment the sensor means comprises a camera adapted to capture image frames in a defined signal space having a multiple spectrum, for instance, RGB, sRGB, Rg traumaticity, HSV, HSL, CMYK, YPbPr, YCbCr, xvYCC, and suchlike.

By way of example, the sensor means can be embodied by conventional digital cameras adapted for recording sequences of images, e.g. by monitoring or observing cameras, for instance in the field of health monitoring or security monitoring, and also by so-called web cams.

In case a special purpose camera is applied, this embodiment can be further developed such that the detector means, the converter means and the sensor means are arranged in a common housing. That is, also the input channel can be disposed in the housing such that an external access thereto is impeded. Hence, the preservation of the desired level of privacy is further enhanced as the input signal cannot be picked up in an unmodified state.

This embodiment is preferably further developed in that the system comprises a buffer means for buffering the input signal, the buffer means comprising an access protection for preventing an unauthorized data access. There are several embodiments of the buffer means, such as software buffers or hardware buffers, e.g. semiconductor memory, such as RAM, ROM, EPROM and the like.

As the buffer means, in principle, is a weak point an unauthorized data access could be addressed to, it is appreciated to apply further measures for protecting the buffer means. Such measures can be embodied as software measures, hardware measures or a combination thereof. A proper software measure could be an encryption of the buffered data. A hardware measure could be embodied by a housing comprising a seal. In a preferred embodiment a breakage of the seal can be detected or, alternatively, leads to a break of a signal line for the input signal.

It could be further advantageous to provide an access control connected to a bypass line, wherein the access controller is adapted to allow, on authorized demand, a direct access to the input signal.

Adapted in this manner, the system can run on two operation modes, namely a privacy preservation mode and an immediate data access mode. The latter mode could be applied, for instance, when special requirements are to be fulfilled. Such requirements could be desirable in cases of epidemics, such as influenza and the like, where the health of a recorded living being is to be assessed. By way of example, typical applications therefor can be envisaged in the field of border controls, health monitoring, or monitoring of public places and public transportation.

According to another preferred embodiment the detector means is further adapted for applying a color normalization and a luminance normalization to the signal space.

This measure serves to further facilitating the detection of the at least one vital signature in the input signal as the degree of freedom in the specific signal space is reduced leading to a simplified extraction.

The color normalization can comprise the detection of time-average values for distinct signal components and the calculation of normalized values of respective color components by applying the time-average values to given actual values of the input signal, e.g. by a moving average calculation wherein actual values are divided by moving average values thereof.

The luminance normalization can comprise a modification of color-representative components of the input signal by applying a defined combination of primary color components thereto. In this way, temporal variations induced by varying illumination conditions can be reduced or even eliminated, e.g. by a division of color-representative components of the input signal by a determined linear combination of primary color components.

When applying both the color normalization and the luminance normalization to the signal space, the problem underlying the detecting of the at least one vital signature can by simplified by a reduction to an algebraic calculation related to fewer dimensions.

In another aspect of the present invention a method for processing data obtained from an input signal is presented, wherein the input signal comprises physiological information derivable from visible radiation reflected by an object, the physiological information being representative of at least one at least partially periodic vital signal, the method comprising:

receiving an input signal from an input channel, detecting at least one vital signature in the input signal, the at least one vital signature varying over time and corresponding to the at least one at least partially periodic vital signal, creating an output signal by modifying the input signal depending on the detected vital signature, wherein the output signal comprises an artificial signature at least partially replacing a respective vital signature of the at least one vital signature of the input signal, and delivering the output signal to an output channel.

Advantageously, the method can be carried out using the system for processing data of the invention.

According to an even further aspect of the invention a computer program is presented, the computer program comprising program code means for causing a computer to carry out the steps of the method for processing data of the invention when said computer program is carried out on a computer.

Preferred embodiments of the invention are defined in the dependent claims. It shall be understood that the claimed method has similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
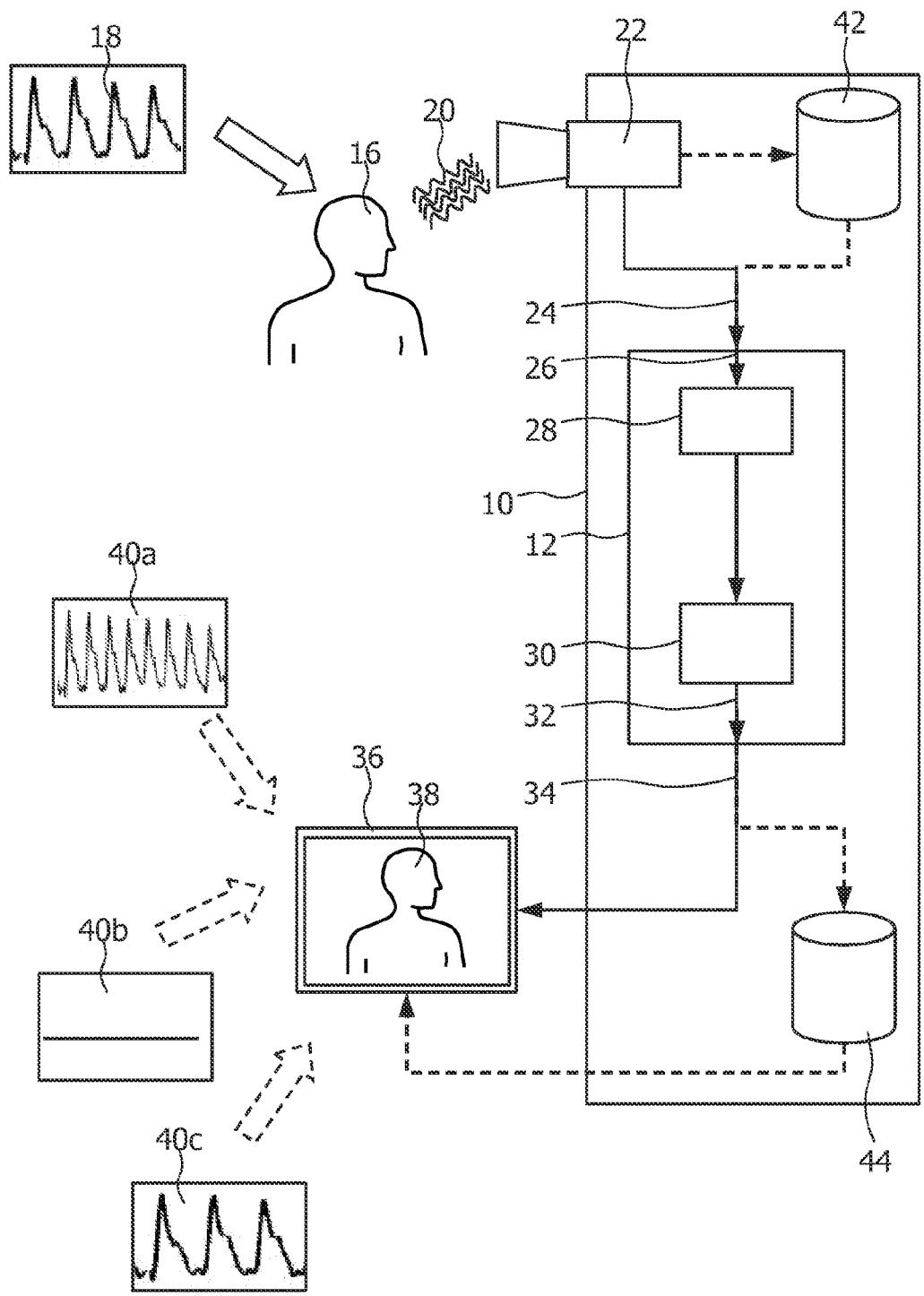
FIG. 1 shows a schematic illustration of a general layout of a system in which the present invention can be used.

Referring to FIG. 1, a system for processing data is illustrated and denoted by a reference numeral 10. The system 10 can be utilized for recording image frames of an object 16. The object 16 can be a human being or animal, or, in general, a living being. For extracting desired information from the recorded data a defined part or portion of the object can be recorded by capturing a series of image frames over time. A proper data base for subsequent image processing can be created in such a way. Several extraction steps can be applied to the collected data, so as to gain a vital signal 18 therefrom, such as heart rate, respiration rate, or heart rate variability. The vital signal 18 can be considered an illustrative example of several vital signals derivable from captured image sequences. As mentioned above, WO 2010/100594 A2 discloses a method of extracting the desired signals by analyzing a sequence of image frames as well as several refinements thereof. It could be demonstrated that even under poor conditions with respect to, by way of example, luminance, color and motion conditions the extraction of the desired signal can be achieved.

However, it is often desired to preserve the privacy of the recorded object 16 in that the extraction of such desired signals is prevented or, at least, impeded to a certain extent while the object 16 is still recognizable. As more and more data is being collected in everyday life, the risk of data abuse also raises accordingly. Potential scenarios in this context can be envisaged with little imagination, e.g., in the field of video interviews, security surveillance or health monitoring. For instance, from video data recorded at a press conference of a politician, it could be possible to retrieve the heart rate of the politician which might then be used to make conclusions on the health status, real thinking or the validity of his statements, which might be undesired. Hence, a possible application for the invention could be to admit only cameras for use in such press conferences that are certified that such conclusions cannot be made, e.g. because the present invention is implemented in said camera to prevent that.

The potentially desired vital signal 18 can be derived from electromagnetic radiation, in particular from visible radiation 20. The desired vital signal 18 can be contained in the visible radiation 20 and, moreover, in electromagnetic radiation in general. Also ultraviolet radiation and infrared radiation can be envisaged besides visible radiation. To this end, it is worth noting that the respective radiation can be reflected or even emitted by the object 16, the latter of which is the case, by way of example, at least partially, when, either in addition or exclusively, detecting infrared radiation.

Needless to say, the system 10 also could be utilized without an integrated sensor means 22 by processing data already captured and stored or buffered.

Taking into consideration the privacy preservation need outlined above, the system 10 is further adapted to process the data which can be derived from the visible radiation 20 recorded by a sensor means 22 and obtainable from an input signal 24. The input signal 24 can be delivered to an input channel 26. The system 10 further comprises a subsystem 12 wherein a detector means 28 and a converter means 30 are disposed. The detector means 28 can be connected to the input channel 26 so as to receive the input signal 24 on demand.

The detector means 28 can be utilized to detect the desired vital signal 18. Hence, the vital signal 18 can be extracted from the input signal 24. However, no external access to the vital signal 18 is provided as the system 10 is merely utilized for a subsequent modification of the input signal 24. Moreover, several access limitations can be utilized in this context at the detector means 28, the converter 30, or, in general, the submeans 12 for privacy preservation measures.

The converter means 30 can be connected to an output channel 32 to which an output signal 34 can be delivered. The converter means 30 is further adapted for creating the output signal 34 by modifying the input signal 24 in that the vital signal 18 cannot be extracted therefrom anymore. Instead, an artificial signal 40 can be extracted from the output signal 34. Hence, the privacy of the recorded object 16 is adequately protected while still allowing a proper representation of the recorded object. The input channel 26 and the output channel 32 can be embodied by a bus system provided with respective interfaces. It goes without saying that the detector means 28 and the converter means 30 can be implemented by means of a processing unit comprising one or more processors.

The output signal 34 comprises at least one processed image frame 36 comprising processed physiological information 38. In the event that an extraction of a desired vital signal (cf. reference numeral 18 in FIG. 1) is applied to the output signal 34, merely an artificial signal 40a, 40b, 40c can be detected. By way of example, the artificial signals 40a, 40b, 40c illustrate alternative modifications applied to the input signal 24. Substantially, the artificial signals 40a, 40c can be considered a proper result of the extraction of the desired signal. However, as the at least one processed image frame 36 comprises "fake information", also the detectable artificial signals 40a, 40c cannot indicate the vital signal 18 originally aimed at. The signal 40a is indicative of a value of interest that is, e.g. when assessing the heart rate, too large by definition while the signal 40c is indicative of a value of interest that is too small by definition.

According to one embodiment, when analyzing the output signal 34, the modification of the original input signal 24 remains concealed. In the alternative, it could be appreciated that the output signal 34 indicates that a modification thereof has been carried out. To this end, when analyzing the output signal 34, an artificial signal 40b can be detected that clearly differs from assumed vital signals. Again, it should be noted that the modification carried out does not necessarily imply that a user is able to realize differences during visual perception when observing a representation of the output signal 34 compared to the original representation of the recorded object 16.

In an alternative embodiment the system 10 further comprises a buffer means 42 and/or a storage means 44 for buffering or storing the input signal 24 and the output signal 34, see also the broken bypass lines in FIG. 1. Hence, besides an instant mode of operation, therefore, also a mediate mode of operation is enabled. Buffering of raw data and processed data, e.g. in a final state or a non-final state, can facilitate the analyzing and modification steps applied to the data. However, it is appreciated if only processed data in the final state is stored and made available for external access.

According to a first overall embodiment the system 10 can be implemented my means of a personal computer connectable to or comprising a camera, the personal computer being driven by suitable program code or logic commands. According to another overall embodiment the system 10 can be implemented by means of a video surveillance system comprising a processing unit driven by suitable program code or logic commands.

Figure 2:
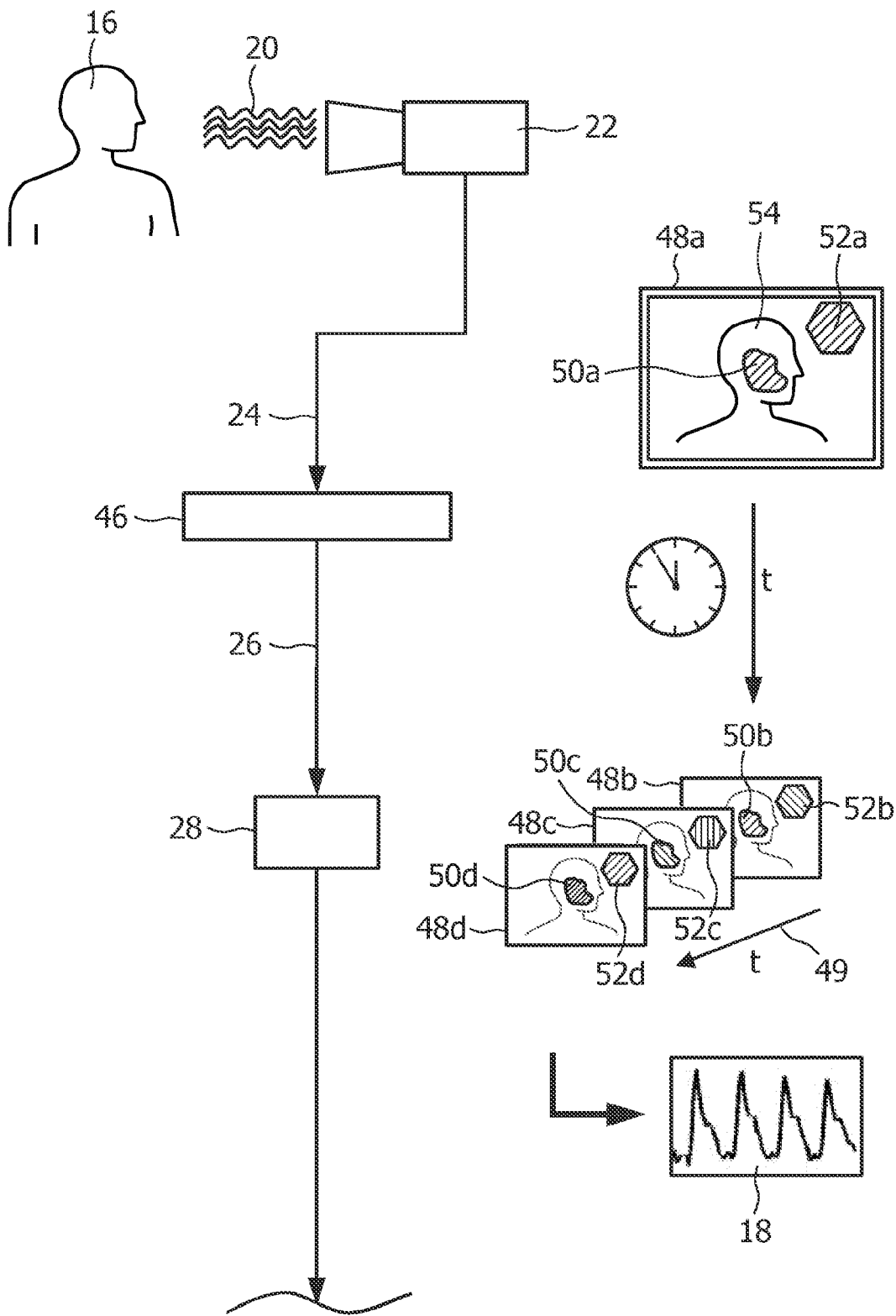
FIG. 2 shows a first part of a block diagram illustrating a first part of an embodiment of a system in which the present invention can be used.
Figure 3:
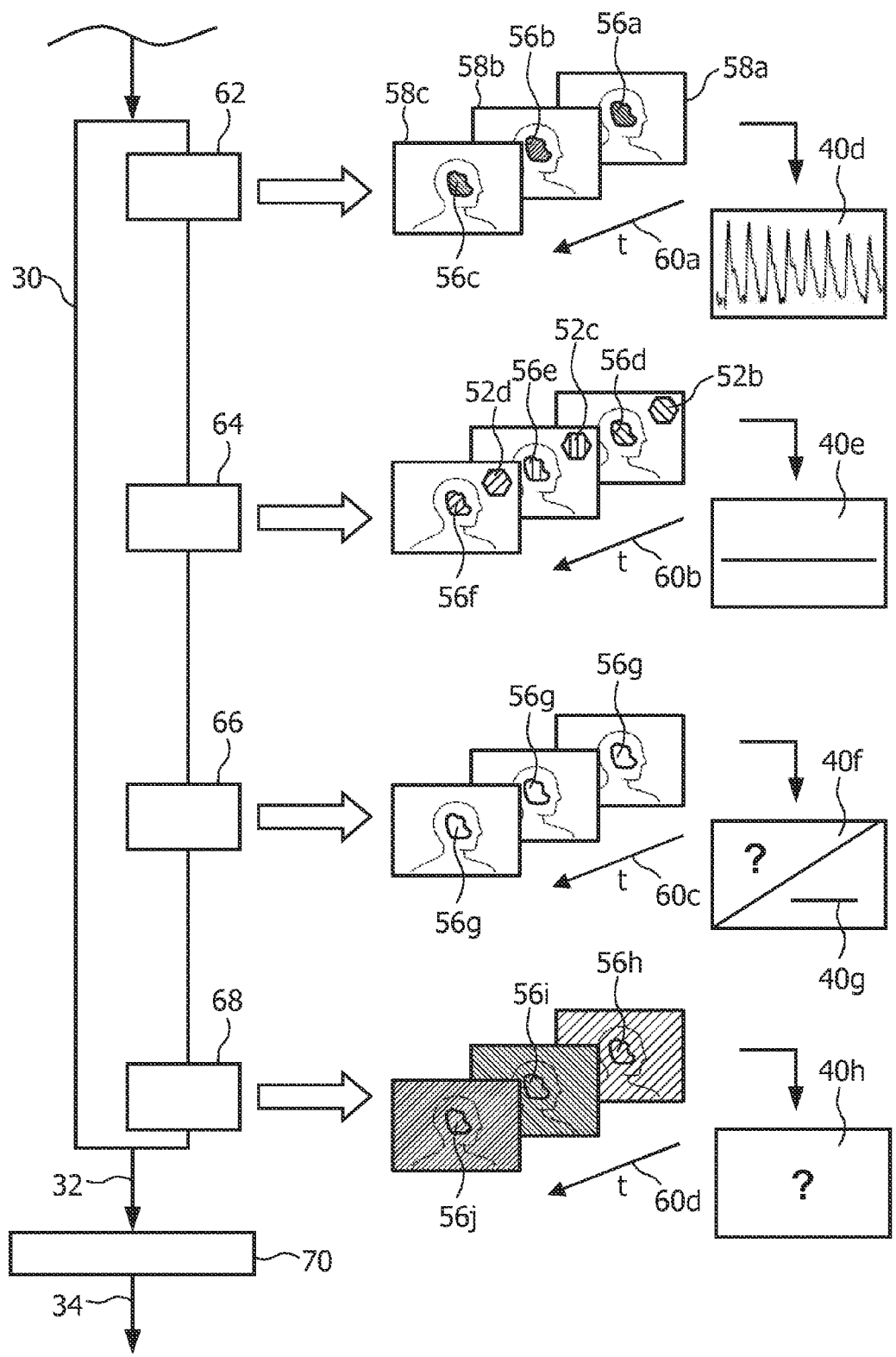
FIG. 3 shows a second part of the block diagram of the embodiment of the system according to FIG. 2.

FIG. 2, which is to be considered in conjunction with FIG. 3, illustrates several sample utilizations of a system for processing data. The sensor means 22, e.g. a video camera or a webcam, is adapted for detecting visible electromagnetic radiation 20 reflected by the object 16. Thus, the sensor means 22 captures the input signal 24, also referred to as raw data. The input signal 24 can be delivered to an interface 46 to which the input channel 26 is attached. Via the interface 46 and the input channel 26 the input signal 24 can be delivered to the detector means 28. Basically, the detector means 28 is adapted to carry out an analysis of the input signal 24 related to the method disclosed in the WO 2010/100594 A2. However, the detector means 28 is not adapted to make the extracted information available to an external unauthorized access.

Reference numeral 48a depicts a sample captured image frame delivered to the detector means 28. The image frame 48a comprises a representation of the object 16 comprising a vital signature 50a which can be drawn for subsequent analyses. As indicated by an arrow t, several captured image frames 48b, 48c, 48d recorded over time and forming an input sequence 49 can be utilized for detecting the vital signal 18. It is required to extract the desired vital signal 18 at least to a certain extent enabling a subsequent modification of the input signal 24 adequately masking, hiding or modulating the vital signal 18 in the output signal 34 made available for external or even public access.

The image frame 48a further comprises a non-indicated signature 52a which is not exposed to temporal variations indicative of the vital signal 18 of the object 16. That is, the non-indicative signature 52a is merely subjected to overall variations and noise generally overlaying the whole image frame 48a. Both a sequence of the vital signature 50b, 50c, 50d and a sequence of the non-indicative signature 52b, 52c, 52d can be compared in a way as to assess the desired vital signal 18. With respect to the detection of the desired signal it is also referred to the still unpublished European Patent application No. 09172337.9, in the name of the same applicant as the present invention. This application depicts further refinements of a signal extraction process suitable for the detection of vital signals from input data.

It goes without saying that, in order to achieve a sufficient preservation of the desired level of privacy, the vital signature 50a is preferably adapted to a whole part of the image frame 48a substantially comprising physiological information 54. It is therefore appreciated that the detection of the vital signature 50a also comprises a detection of relevant parts of the image frame 48a indicative of vital signals in general. To this end, by way of example, the respective relevant parts can be formed by skin tone pixels contained in the image frame 48a. However, in the alternative, it can be envisaged that merely a subpart of the respective relevant part is drawn for the detection of the vital signal as long as it is ensured that the whole respective relevant part is to be modified during a subsequent modification carried out by the converter means 30, see FIG. 3. In this context, it should be noted that, for illustrative purposes, the respective relevant areas such as the vital signature 50 (and also an artificial signature 56) provided in the figures does not cover the whole potentially indicative area of the respective sample object 16.

In other words, when recording, by way of example, the face of an object 16 the whole area of the face should be modified accordingly. In regard of a more detailed explanation of the method underlying the detection of the at least one vital signature 50 and of temporal variations thereof, it is referred to further statements set out below in conjunction with FIG. 6, and to WO 2010/100594 A2 as well as to EP application No. 09172337.9.

Turning towards FIG. 3, the creation of the output signal 34 by modifying the input signal 24 depending on the detected vital signature 50 is illustrated. By way of example, the converter means 30 may comprise a modulator means 62, a leveling means 64, a mask means 66 and an overall converter 68. Needless to say, the converter means 30 alternatively may comprise merely one, two or three of the respective subdevices.

The modulator means 62 is adapted for modifying the temporal variations of the at least one vital signature 50. After applying the conversion, the output signal 34 comprises an output sequence 60a of output image frames 58a, 58b, 58c wherein an artificial signature 56a, 56b, 56c is embedded. Temporal variations of the artificial signature 50a, 50b, 50c are indicative of an artificial signal 40d. When comparing the original vital signal 18 and the resulting artificial signal 40d, it becomes clear that a frequency modification has been carried out. Consequently, an unauthorized extraction of a desired vital signal will result in the artificial signal 40d no longer indicative of the original vital signal 18.

In another embodiment a leveling means 64 may be applied that is adapted to level the temporal variations of the at least one vital signature 50. It should be understood that the term "leveling" may comprise an alignment thereof with overall temporal variations of a non-indicative signature 52 of a captured image frame 48. In FIG. 3 both the sequence of the non-indicative signature 52b, 52c, 52d and the sequence of the artificial signature 56d, 56e, 56f coincide to such an extent that, when an analysis is applied to the output sequence 60b to detect temporal variations of the at least one assumed "vital signature" (i.e., the artificial signature 56d, 56e, 56f), merely a leveled artificial signal 40e can be extracted therefrom. Thus, the artificial signal 40e cannot be utilized for obtaining personal information about the object 16. In FIG. 3, by means of illustration, the pattern of both the non-indicative signature 52b, 52c, 52d and the pattern of the artificial signature 56d, 56e, 56f are aligned in each frame of the output sequence 60b. In this regard, it is emphasized that the sequence of the non-indicative signature 52b, 52c, 52d basically remains unchanged with respect to the sequence of captured image frames 48b, 48c, 48d.

In this connection, it can be envisaged that, when applying an unauthorized analysis to the extracted artificial signal 40e, the used detector can be further adapted for detecting the fact that a desired vital signal is replaced by an artificial signal 40e. But, however, such a method and the algorithm underlying the method cannot "restore" the vital signal 18 from the artificial signal 40e.

In another embodiment the converter means 30 may comprise a mask means 66 which is adapted for removing the at least one vital signature 50 from the input signal 24. The mask means 66 can be further adapted to replace the respective vital signature 50b, 50c, 50d by a substantially steady artificial signature 56g. The artificial signature 56g may be constant over time. As mentioned above, hence, the result can be an impression comparable to a "china doll" skin color. Thus, when applying an analysis to the output sequence 60c substantially characterized by the steady artificial signature 56g constant over time either, when comparing temporal variations of the artificial signature 56g (i.e., hardly detectable or even undetectable variations of the artificial signature 56g) with noise-induced variations of a non-indicative signature 52, it can be detected, as a possible result, an artificial signal 40f clearly indicating an error of the analysis or an artificial signal 40g indicating that merely minor or even no temporal variations at all could be extracted.

By way of a further alternative embodiment FIG. 3 illustrates an overall converter 68 for varying a major portion of the image frames, wherein a destructive modulation can be applied to the temporal variations of the at least one vital signature 50b, 50c, 50d. As illustrated by the patterns covering each output image frame of the output sequence 60d, a major portion of the, or even the whole image frame can be modified in this way. So, besides the artificial signatures 56h, 56i, 56j, also the remaining parts of each frame can be subjected to the modulation. The modulation can also comprise random elements for carrying out a random multi-mixing of image elements of output image frames of the output sequence 60d. Hence, when subjecting the output sequence 60d to an analysis so as to determine temporal variations of the at least desired vital signature 50, eventually merely an artificial signal 40h can be derived therefrom clearly indicating an error.

Again, it should be noted that preferably, even if an overall modification is carried out to a certain extent sufficient for replacing the original vital signal 18, these modifications do not become obvious to a human observer.

The processes data, namely the output signal 34 can be made available at a data access interface 70 to which the output channel 32 can be connected.

Figure 4:
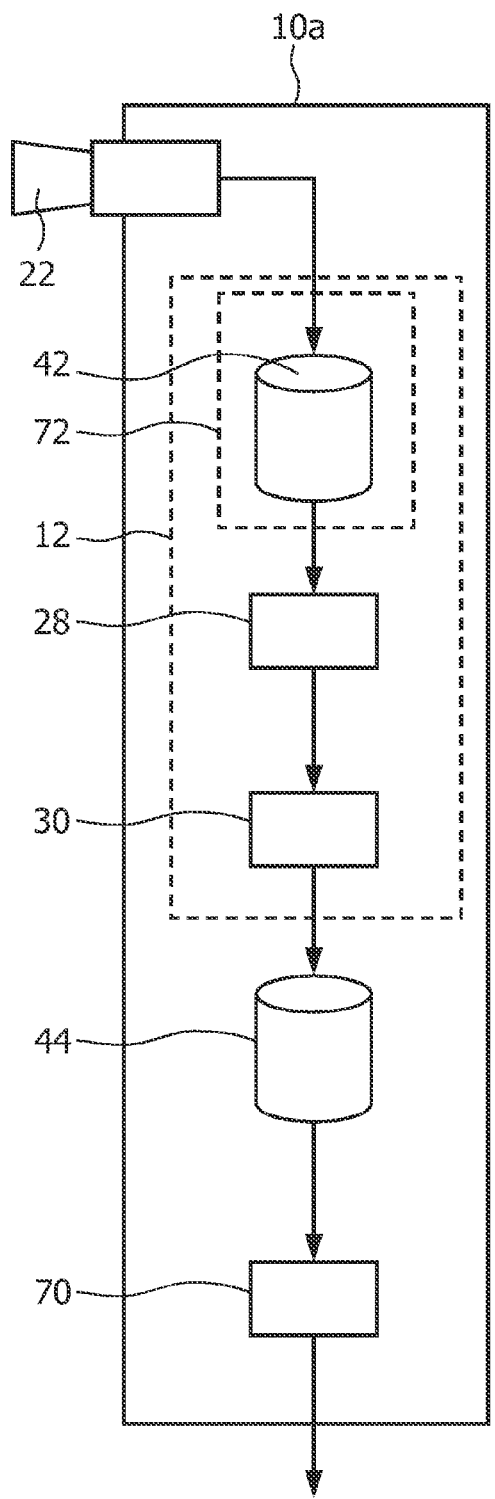
FIG. 4 shows a schematic block diagram of an embodiment of a system according to the present invention.
Figure 5:
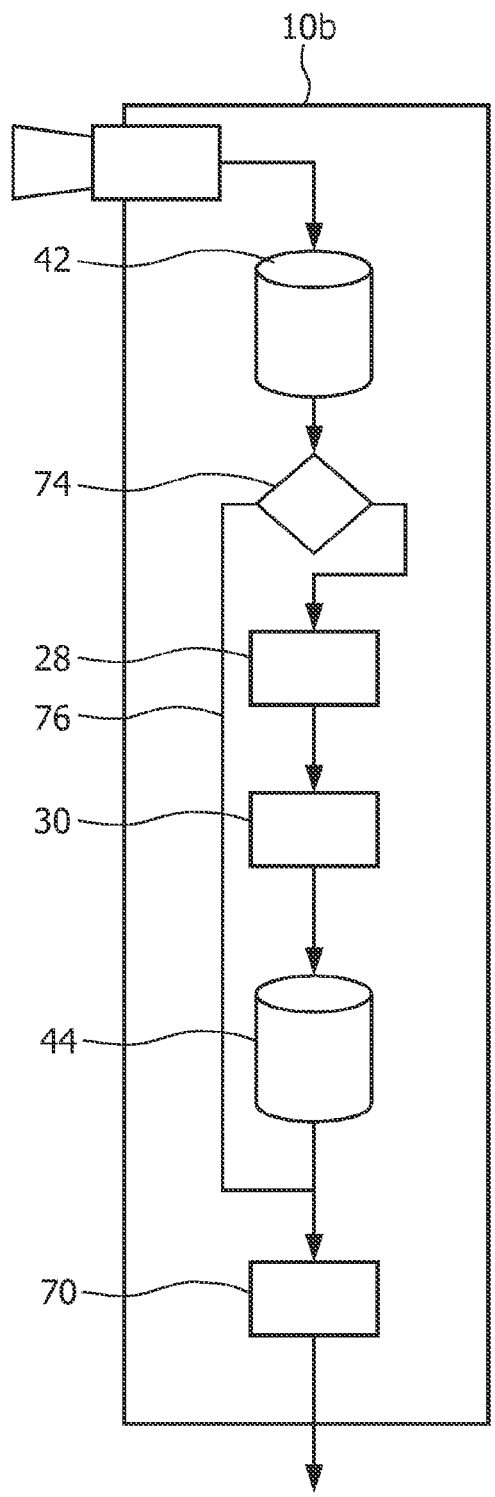
FIG. 5 shows a further schematic block diagram of another embodiment of a system according to the present invention.

Referring to FIG. 4 and FIG. 5, two alternative embodiments of systems 10a, 10b for processing data are illustrated. Both systems 10a, 10b comprise a sensor means 22, a buffer means 42, a detector means 28, a storage means 44, and a data access interface 70.

However, the system 10a further comprises an enhanced level of privacy preservation as, firstly, the buffer means 42, the detector means 28, and the converter means 30 are arranged in a subsystem 12, while, secondly, the buffer means 42 is further surrounded by an access protection 72. It can be envisaged that also the sensor means 22 is covered by the subsystem 12 or the access protection 72.

As shown in FIG. 4, the main components of the system 10a subjected to unauthorized data access are disposed in the subsystem 12 such that an unauthorized access is impeded to a certain level. Further, the component most susceptible to an unauthorized access, namely the buffer means 42, can be hermetically housed in order to prevent unauthorized mechanical or electronic access.

In contrast, the system 10b is adapted to operate in two operation modes, namely a first, privacy preservation mode and a second, raw data access mode. To this end, an access control 74, substantially providing a switching function, is arranged between the buffer means 42 and the detector means 28. In the first operation mode the access control couples the buffer means 42 with the detector means 28 so that the input signal 24 can be delivered thereto. In the second mode the access control couples the buffer means 42 via a bypass 76 to the data access interface 70. Thus, the input signal 24 can bypass the detector means 28 and the converter means 30 and can be made available to external data access via the data access interface 70. It is worth noting that, in this embodiment, the authority to actuate the access control 74 should be limited to special events or incidents and, moreover, restricted to a considerably small trustful group of users.

Figure 6:
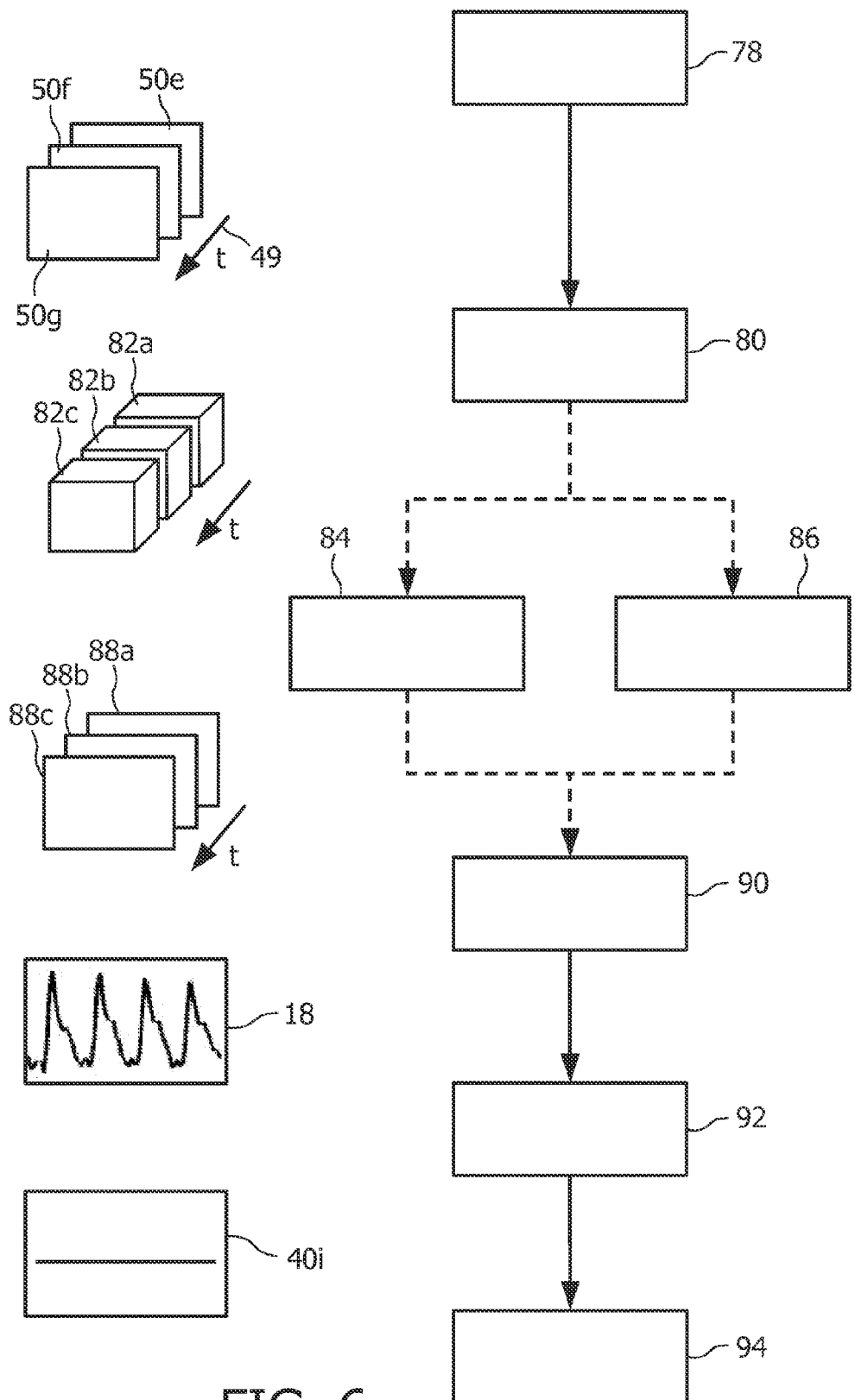
FIG. 6 shows a block diagram illustrating several steps of an embodiment of a method according to the present invention.

FIG. 6 schematically illustrates a method for processing data. Initially, in a step 78 data is received or acquired. The data can be delivered from a sensor means 22 or a buffer means 42. In a subsequent step 80 at least one vital signature 50e, 50f, 50g is detected in an input sequence 49 of the input signal. As an advantageous supplement, as indicated by broken arrows, a color normalization 84 and/or a luminance normalization 86 can be applied to a set of signal spaces 82a, 82b, 82c wherein the desired variations indicative of temporal variations of the detected vital signatures 50e, 50f, 50g can be depicted. Consequently, the problem of extracting a vital signal 18, illustrated by a step 90, can be facilitated, by way of example, in that a multi-dimensional problem can be transferred to a two-dimensional problem as indicated by the normalized signal spaces 88a, 88b, 88c. It goes without saying that the steps 84 and 86 alternatively may follow or precede each other.

After having extracted the relevant information, namely the vital signal 18 indicative of personal information to be preserved, this information can be utilized for modifying the input signal, step 92, in a way as to merely allow the extraction of an artificial signal 40i therefrom. Eventually, the modified output signal can be delivered and distributed, step 94.

Figure 7:
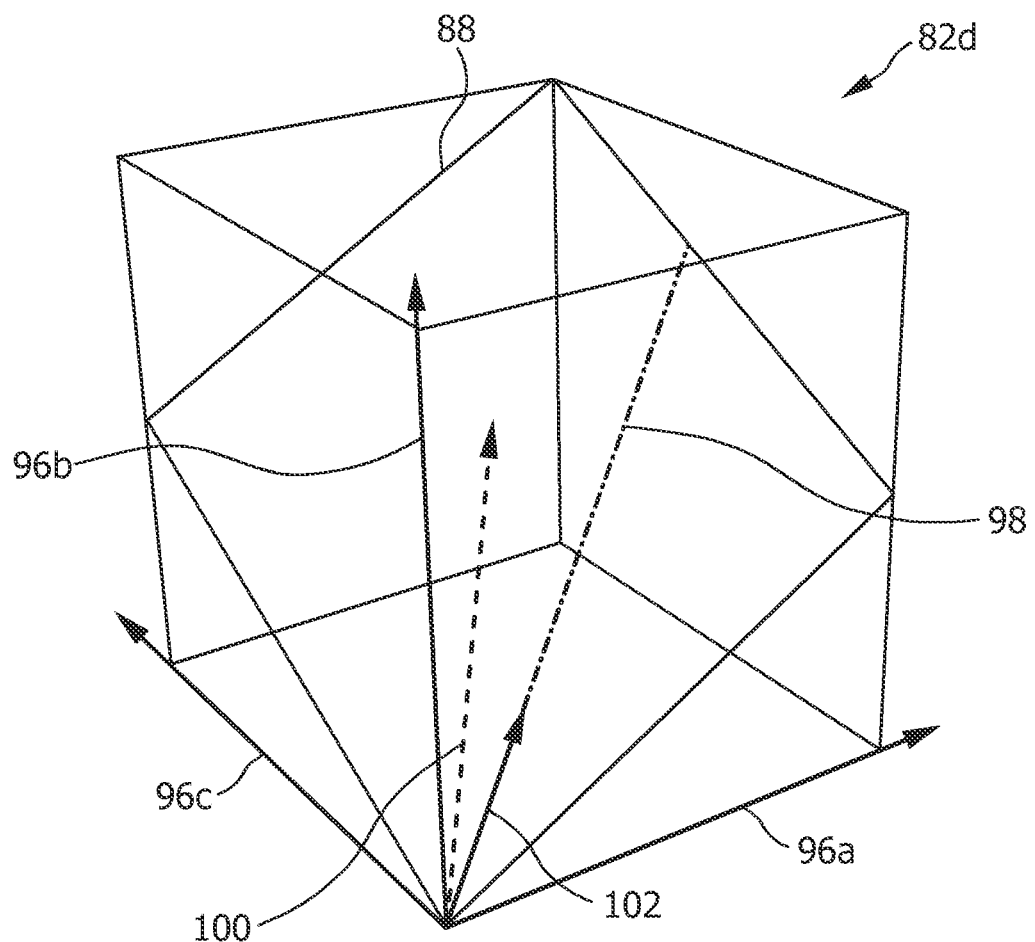
FIG. 7 shows a sample schematic illustration of a signal space to which a normalization can be applied.

FIG. 7, by way of example, illustrates a luminance normalization applied to a sample signal space 92d. The signal space 92d can be considered a RGB space having three axes 96a, 96b, 96c, each respective of a distinct main color value. To this signal space 82d a luminance normalization is applied by a determined linear combination of single values (e.g., R-value+G-value+B-value=constant) leading to a dimensional reduction of the underlying problem. Thus, a normalized signal space 88 resulting therefrom can be considered a plane. The normalized signal space comprises a heart beat axis 98 which can be determined empirically by approximative measures. A detected signal 100 is representative of temporal variations of an at least one vital signature. However, besides the vital component, the detected signal 100 is also representative of overall temporal variations, such as noise and the like, overlaying a captured image frame. By projecting the detected signal 100 to the predetermined heart beat axis 98 a projected signal 102 indicative of a temporal value of the desired vital signal can be estimated avoiding disturbing components having a perpendicular orientation with respect to the heart beat axis 98.

In this context it is worth noting that the sample signal space 82d illustrates actual difference values representative of the temporal variations of interest. A color normalization carried out consecutively to or before the luminance normalization can further contribute facilitating the extraction of the desired vital signal.

Hence, the vital signal can be extracted from the input signal, and, moreover, utilized for modifying the input signal in order to preserve privacy information. After being subjected to the modification, merely a "fake signal" can be detected having a length and orientation clearly different from a length and orientation of the detected signal 100. Thus, the vital signal cannot be restored.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A privacy system for processing data obtained from an input signal comprising physiological information derived from radiation reflected by a person, the physiological information being representative of at least one vital signal of the person, the system comprising:
   a detector configured to detect at least one vital signature in the input signal, wherein the input signal comprises a continuous or discrete sequence of image frames related to a specific signal space, the at least one vital signature varying over time and corresponding to variations of the at least one vital signal, and wherein the at least one vital signal is obtained from variations of skin color over time; and
   a converter configured to create an output signal by modifying the input signal depending on the detected vital signature,
   wherein the output signal comprises an artificial signature at least partially replacing a respective vital signature portion of the at least one vital signature of the input signal.

2. The privacy system as claimed in claim 1, wherein the continuous or discrete sequence of image frames comprises a representation of the person, the representation of the person comprising the at least one vital signature, wherein the at least one vital signal is at least a partially periodic vital signal of the person, and wherein the detector is further configured to detect temporal variations of the at least one vital signature, the temporal variations of the at least one vital signature corresponding to temporal variations of at least partially periodic vital signal.

3. The privacy system as claimed in claim 2, wherein the converter includes one of a leveler configured to level the temporal variations of the at least one vital signature, a mask configured to remove the at least one vital signature from the input signal, an evaluation facilitator configured to enhance an amplitude of the vital signal, and a modulator configured to apply a frequency modification to the temporal variations.

4. The privacy system as claimed in claim 2, wherein the converter is an overall converter for varying a major portion of the image frames, the major portion comprising the at least one vital signature and a non-indicative signature, and wherein the overall converter is configured to apply a destructive modulation to the temporal variations of the at least one vital signature.

5. The privacy system as claimed in claim 4, further comprising a buffer configured to buffer the input signal, wherein access to the buffer is provided through an access protector configured to prevent an unauthorized access of data stored in the buffer.

6. The privacy system of claim 5, wherein the access protection includes a first housing configured to house the buffer, the detector and the converter, and the access protection further including a second housing configured to hermetically house the buffer.

7. The privacy preservation system as claimed in claim 2, wherein the converter is further configured to apply a multi stage conversion to the at least one vital signature.

8. The privacy system as claimed in claim 1, further comprising a sensor configured to detect the radiation within at least one particular wavelength range selected from the group consisting of visible light, infrared light, and ultraviolet radiation, the sensor being connectable to the input channel.

9. The privacy system as claimed in claim 1, wherein the detector is further configured to apply a color normalization and a luminance normalization to the signal space.

10. The privacy system of claim 1, wherein the continuous or discrete sequence of image frames comprises a representation of the person, the representation of the person comprising the at least one vital signature, wherein the at least one vital signal is at least a partially periodic and is selected from a group consisting of heart rate, respiration rate, and heart rate variability.

11. The privacy system of claim 1, wherein the converter is configured to receive the at least one vital signature from the detector and to create the artificial signature by modifying the at least one vital signature.

12. A privacy preservation method for processing data obtained from an input signal comprising physiological information derived from radiation reflected by a person, the physiological information being representative of at least one vital signal of the person, the method comprising acts of:
   receiving an input signal from an input channel;
   detecting by a detector at least one vital signature in the input signal, wherein the input signal comprises a continuous or discrete sequence of image frames related to a specific signal space, the at least one vital signature varying over time and corresponding to variations of the at least one vital signal, and wherein the at least one vital signal is obtained from variations of skin color over time;
   creating by a converter an output signal by modifying the input signal depending on the detected vital signature, wherein the output signal comprises an artificial signature at least partially replacing a respective vital signature of the at least one vital signature of the input signal; and
   delivering the output signal to an output channel.

13. The privacy preservation method of claim 12, wherein the continuous or discrete sequence of image frames comprises a representation of the person, the representation of the person comprising the at least one vital signature, wherein the at least one vital signal is at least a partially periodic and is selected from a group consisting of heart rate, respiration rate, and heart rate variability.

14. The privacy preservation method of claim 12, wherein the creating act further comprises creating the artificial signature by modifying the at least one vital signature of the input signal.

15. The privacy preservation method of claim 12, wherein the creating act modifies the at least one vital signature of the input signal by at least one of:
   leveling temporal variations of the at least one vital signature,
   removing the at least one vital signature from the input signal,
   enhancing an amplitude of the vital signal, and
   applying a frequency modification to the temporal variations.

16. The privacy preservation method of claim 12, wherein the converter is an overall converter for varying a major portion of the image frames, the major portion comprising the at least one vital signature and a non-indicative signature, and wherein the overall converter is configured to apply a destructive modulation to temporal variations of the at least one vital signature.

17. A non-transitory computer readable medium comprising computer instructions which, when executed by a processor, configure the processor to perform a privacy preservation method for processing data obtained from an input signal comprising physiological information derived from radiation reflected by person, the physiological information being representative of at least one vital signal of the person, the method comprising acts of:

receiving an input signal from an input channel;

determining at least one vital signature in the input signal, wherein the input signal comprises a continuous or discrete sequence of image frames related to a specific signal space, the at least one vital signature varying over time and corresponding to variations of the at least one vital signal, and wherein the at least one vital signal is obtained from variations of skin color over time;

creating an output signal by modifying the input signal depending on the determined vital signature, wherein the output signal comprises an artificial signature at least partially replacing a respective vital signature of the at least one vital signature of the input signal; and delivering the output signal to an output channel.

18. The non-transitory computer readable medium of claim 17, wherein the continuous or discrete sequence of image frames comprises a representation of the person, the representation of the person comprising the at least one vital signature, wherein the at least one vital signal is at least a partially periodic and is selected from a group consisting of heart rate, respiration rate, and heart rate variability.

19. The non-transitory computer readable medium of claim 17, wherein the creating act further comprises creating the artificial signature by modifying the at least one vital signature of the input signal.

20. The non-transitory computer readable medium of claim 17, wherein the creating act modifies the at least one vital signature of the input signal by at least one of:

leveling temporal variations of the at least one vital signature, removing the at least one vital signature from the input signal, enhancing an amplitude of the vital signal, and applying a frequency modification to the temporal variations.

\* \* \* \* \*